US008874233B2

(12) United States Patent
McLaughlin et al.

(10) Patent No.: US 8,874,233 B2
(45) Date of Patent: Oct. 28, 2014

(54) DISTRIBUTED NEURO-MODULATION SYSTEM WITH AUXILIARY STIMULATION-RECORDING CONTROL UNITS

(71) Applicant: The Charles Stark Draper Laboratory, Inc., Cambridge, MA (US)

(72) Inventors: Bryan McLaughlin, Cambridge, MA (US); John Lachapelle, Princeton, MA (US); Tirunelveli S. Sriram, Acton, MA (US); Brian Smith, Cambridge, MA (US)

(73) Assignee: The Charles Stark Draper Laboratory, Inc., Cambridge, MA (US)

( * ) Notice: Subject to any disclaimer, the term of this patent is extended or adjusted under 35 U.S.C. 154(b) by 0 days.

(21) Appl. No.: 13/786,329

(22) Filed: Mar. 5, 2013

(65) Prior Publication Data

US 2014/0257434 A1    Sep. 11, 2014

(51) Int. Cl.
*A61N 1/05* (2006.01)
*H01B 7/00* (2006.01)
*A61N 1/36* (2006.01)

(52) U.S. Cl.
CPC ...  *A61N 1/36* (2013.01); *H01B 7/00* (2013.01)
USPC ........................................... 607/116; 607/148

(58) Field of Classification Search
None
See application file for complete search history.

(56) References Cited

U.S. PATENT DOCUMENTS

| | | | |
|---|---|---|---|
| 4,628,934 A | 12/1986 | Pohndorf et al. | |
| 5,470,348 A | 11/1995 | Neubauer et al. | |
| 6,254,525 B1 | 7/2001 | Reinhardt et al. | |
| 6,671,550 B2 * | 12/2003 | Iaizzo et al. | 607/27 |
| 7,212,867 B2 | 5/2007 | Van Venroo et al. | |
| 7,637,867 B2 | 12/2009 | Zdeblick | |
| 7,974,705 B2 | 7/2011 | Zdeblick et al. | |
| 8,024,049 B1 | 9/2011 | Gilson et al. | |
| 2003/0149456 A1 | 8/2003 | Rottenberg et al. | |
| 2005/0033370 A1 | 2/2005 | Jelen et al. | |
| 2005/0070971 A1 | 3/2005 | Fowler et al. | |
| 2006/0265039 A1 | 11/2006 | Bartic et al. | |
| 2007/0129770 A1 | 6/2007 | Younis | |

(Continued)

FOREIGN PATENT DOCUMENTS

| | | |
|---|---|---|
| WO | 2012056039 A1 | 5/2012 |
| WO | 2012091848 A2 | 7/2012 |

OTHER PUBLICATIONS

Feili et al., "Matrix-addressable, active electrode arrays for neural stimulation using organic semiconductors-cytotoxicity and pilot experiments in vivo," J. Neural. Eng. 5(1):68-74 2008.

(Continued)

*Primary Examiner* — Brian T Gedeon
(74) *Attorney, Agent, or Firm* — Lando & Anastasi, LLP

(57) ABSTRACT

Systems and methods for modulating a physiological process are provided to enable precise delivery of signals to a predetermined treatment site. The systems may comprise an implantable device and an electrical lead body. The electrical lead body may comprise a plurality of transducer contacts in close proximity to an end of the electrical lead body, and a control unit positioned within the lead body in close proximity to the plurality of transducer contacts.

17 Claims, 5 Drawing Sheets

(56) References Cited

U.S. PATENT DOCUMENTS

| | | |
|---|---|---|
| 2010/0100152 A1 | 4/2010 | Martens et al. |
| 2010/0137944 A1 | 6/2010 | Zhu |
| 2010/0198315 A1 | 8/2010 | Martens et al. |
| 2010/0292629 A1 | 11/2010 | Dacey, Jr. et al. |
| 2010/0305664 A1 | 12/2010 | Wingeier et al. |
| 2011/0190860 A1 | 8/2011 | Harberts et al. |
| 2011/0301665 A1 | 12/2011 | Mercanzini et al. |
| 2012/0035684 A1 | 2/2012 | Thompson et al. |
| 2012/0109262 A1 | 5/2012 | Martens |
| 2012/0283800 A1 | 11/2012 | Perryman et al. |

OTHER PUBLICATIONS

Ramachandran et al., "Design, in vitro and in vivo assessment of a multi-channel sieve electrode with integrated multiplexer," J. Neural. Eng., 3(2):1:114-24, 2006.

Schuettler et al., "Multichannel neural cuff electrodes with integrated multiplexer circuit," 1st Annual International on Microtechnologies in Medicine and Biology, Oct. 12-14, 2000, p. 624-9.

International Search Report and Written Opinion dated Apr. 25, 2014 for PCT Application No. PCT/US2014/020011.

\* cited by examiner

DISTRIBUTED NEURO-MODULATION SYSTEM WITH AUXILIARY STIMULATION-RECORDING CONTROL UNITS

FIELD OF THE DISCLOSURE

This disclosure relates to systems and methods of modulating a physiological process. More particularly, this disclosure relates to systems and methods of modulating a physiological process to enable precise delivery of signals to a predetermined treatment site.

SUMMARY

In some embodiments of the present disclosure, a physiological electrical lead body is provided. The physiological electrical lead body may comprise a plurality of transducer contacts in close proximity to an end of the electrical lead body and a control unit. The control unit may be positioned within the lead body in close proximity to and in communication with the plurality of transducer contacts. The control unit may be constructed and arranged to enable precise delivery of signals to a predetermined treatment site. The control unit may comprise at least one electrical input contact, and a plurality of electrical output contacts, wherein a quantity of the electrical output contacts is greater than a quantity of the electrical input contacts.

In some other embodiments of the present disclosure, a system for modulating a physiological process is provided. The system may comprise an implantable device comprising an energy source. The implantable device may be constructed and arranged to provide a signal. The system may also comprise an electrical lead body connected to the implantable device. The electrical lead body may comprise a plurality of transducer contacts in close proximity to an end of the electrical lead body, and a control unit positioned within the lead body in close proximity to the plurality of transducer contacts. The control unit may be constructed and arranged to enable precise delivery of signals to a predetermined treatment site. The control unit may comprise at least one electrical input contact and a plurality of electrical output contacts, wherein a quantity of the electrical output contacts is greater than a quantity of the electrical input contacts.

In some other embodiments of the present disclosure, a method of treating a condition in a subject is provided. The method may comprise generating a first input signal from an implantable device. The method may also comprise transmitting the first input signal from the implantable device to a control unit positioned in an electrical lead body comprising a first end and a plurality of transducer contacts in close proximity to the first end. The method may also comprise generating a plurality of output signals based on the first input signal from the implantable device and on a control function of the control unit. The method may also comprise transmitting the plurality of output signals from the control unit to the plurality of transducer contacts to provide a precise delivery of signals to a predetermined treatment site.

DESCRIPTION OF THE DRAWINGS

The accompanying drawings are not intended to be drawn to scale. In the drawings, each identical or nearly identical component that is illustrated in the various figures is represented by a like numeral. For purposes of clarity, not every component may be labeled in every drawing.

In the drawings.

DETAILED DESCRIPTION

Figure 1:
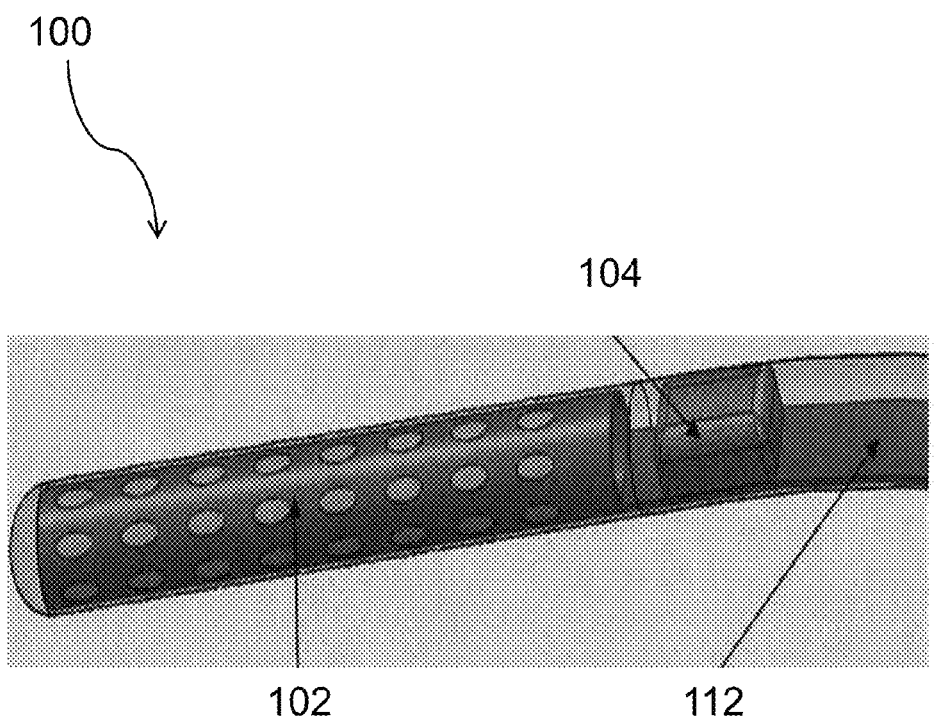
FIG. 1 is an illustration of an electrical lead body in accordance with one or more aspects of the disclosure.

Systems and methods for modulating a physiological process are provided. The systems and methods may provide a more effective technique for neurostimulation or neuromodulation therapies. The systems and methods may be used for neurostimulation or neuromodulation in spinal cord, vagus nerve, deep-brain, and retinal applications. The systems and methods may provide improved therapy or treatment by more tightly controlling or confining a signal or an electrical current to a desired location, such as a target location, treatment area, or treatment site. The desired location or target location may be a location on a subject. The location may be a specific area of tissue. The systems and methods may provide for more tightly controlling or confining one or more electrical currents or signals from stimulus waveforms to a targeted tissue area or volume. The systems and methods may also provide for prevention or reduction of signals or electrical current from reaching undesired or non-targeted areas or volumes.

The systems and methods of the present disclosure may be utilized alone or in combination with a larger system that may be used for physiological treatment or for diagnostic purposes. The systems and methods of the present disclosure may be utilized to gather information or treat a subject over a predetermined period of time, or may be used indefinitely to monitor or treat a subject. It may be used to monitor a subject, or control a physiological condition of a subject, or induce or block a certain physiological event. One or more components of the systems and methods of the present disclosure may be used in a wireless configuration.

The systems and methods of the present disclosure also allow for electrical current to be provided through a greater number of transducer contacts. This allows for a finer adjustment of the electrical current by having a larger number of transducer contacts available to deliver the electrical current and be in contact with the target location of a subject. For example, the present disclosure may allow for electrical current or signals to be provided by having a greater number of transducer contacts over the same surface area as a conventional system having a given number of transducer contacts. The subject may be an animal subject, for example a mammalian subject, or a human subject.

In some embodiments, this may be accomplished by using a controller or control unit as presently disclosed. The control unit may enable the availability of a larger number of transducer contacts to deliver the electrical current or signals and be in contact with the target location of a subject. The control unit may direct incoming stimulus waveforms from a number of input wires or filaments, that are in communication with a device such as an implantable device, to a number of output wires or filaments that deliver electrical current or other signals to a number of transducer contacts. The number of output wires or filaments from the control unit that deliver current to a number of transducer contacts is typically greater than the number of input wires or filaments. In certain examples, the number of input wires or filaments from the device to the control unit may be between 4 and 8 wires or filaments. In these examples, the number of output wires or filaments from the control unit to the transducer contacts may be between 16 and 64 or more. In conventional systems prior to this disclosure it was only possible to provide 4 to 16 input wires, and a corresponding 4 to 16 output wires, leading to a corresponding 4 to 16 transducer contacts. At least one of the limiting factors in conventional systems is the diameter or width of the electrode lead, which in certain systems may be about 2.0 mm or about 1.3 mm, and in some systems 1.27 mm. In certain applications, the diameter or width of the electrode lead is controlled by the incision site and area through which the transducer contacts must be introduced.

The control unit may provide for the ability to have a greater number of output wires or filaments than input wires or filaments. This may be accomplished by including or positioning the control unit in the lead body. This is in contrast to conventional systems in which the control unit is typically embedded or positioned within a pulse generator or implantable device that is separate from the lead body. The control unit may be positioned within the lead body in close proximity to the transducer contacts, at the distal end of the lead body. By positioning the control unit in close proximity to the transducer contacts, it is possible to use filaments of smaller diameter due to the short distance between the control unit and the transducer contacts. This allows for accommodation of a larger number of filaments and permits a greater number of transducer contacts to be present on the lead body. In conventional systems, filaments of smaller diameter may not be used due to the longer distance that they must travel, which causes the smaller diameter wires to be less robust and unpredictable in their operability.

The control unit may be configured to receive control signals and send control signals. For example, the control unit may be configured to receive input control signals and send output control signals. The number of output control signals may be greater than the number of input control signals. The input control signals may be sent from a device that generates at least one signal. The device may be a medical-related device that supplies input signals to the control unit. The device may comprise a pulse generator. The device may also comprise an energy source to energize the pulse generator. In some embodiments, the control unit may be constructed and arranged to derive its energy from the energy source of the device. In one embodiment, the energy source of the implantable device is a battery.

The device may be an implantable device. The device may be at least partially implantable into a subject, such as a human or other mammal. For example, the device may be implantable in the chest region of a subject. The device may be surgically put in place, and may also be surgically removable. At least one of the input control signal and the output control signal may be in the form of a waveform, such as a stimulus waveform. The control unit may provide at least one of power harvesting, electrical stimulus generation, optical stimulus generation, pulse generation, pulse shaping, pulse pass-through, multiplexing, charge balance shaping, and impedance measurement or sensing to measure therapy effectiveness (for example, charge delivery). The control unit may be configured to harvest power from the implantable device to energize the control unit. The implantable device may provide at least a portion of the power to the control unit to energize the control unit. In certain embodiments, the implantable device may provide the power to the control unit to energize the control unit.

The control unit may be configured to send at least one electrical signal to at least one transducer contact at a distal end of the lead body. The control unit may be configured to send at least one electrical signal to each of the transducer contacts at a distal end of a lead body. The transducer contacts, in this example, may be electrodes. The control unit may also be configured to send at least one optical signal to each of the transducer contacts at a distal end of a lead body. The transducer contacts in this example, may be optical output sites. These may be used in applications such as optical excitation or modulation, more specifically, optical neuromodulation or optogenetic modulation.

The control unit may also provide closed loop control using transducer sensing to modify control and stimulation functions. The control unit may send at least one output control signal to at least one transducer contact. The transducer contact may then transmit at least one input signal to the control unit. The control unit may then further send at least one output signal to at least one transducer contact, based on the at least one input signal. The control unit may also send the at least one output signal to at least one transducer contact based on a control function of the control unit.

The control unit may also be capable of performing decision making. The control unit may be configured to communicate or send signals back to the device, for example, the implantable device. In addition or in the alternative, the control unit may be configured, to receive signals from the device. The control unit may also be configured to communicate or send signals to the transducer contacts. In addition or in the alternative, the control unit may be configured to receive signals from the transducer contacts.

Power to the control unit may be harvested from the implantable device. The power may be applied using lead wires between the implantable device and the control unit. In certain embodiments, AC-coupled only signals may be used to ensure or reduce damage due to any wire breakage or leakage, or any other event that may cause tissue damage if a DC signal were to be applied. Power may also be provided wirelessly. This may be accomplished using coupled radio-frequency antennas or acoustic transducers.

In certain embodiments the control unit may be a biocompatible by an integrated ultra high density integrated circuit-based device. The control unit may be enclosed or encapsulated by a material, such as a thin-film hermetic material, that may provide a hermetic seal. The control unit may also comprise hermetic feedthroughs at a high density of, for example, greater than 10 feedthroughs/mm$^2$. The material may be a bio-compatible material. The material may be deposited using a sputtering or atomic layer deposition process. The contacts of the control unit and the input and output locations may also be composed of bio-compatible materials.

Typically, conventional equipment used in the applications disclosed may comprise a titanium enclosed implantable medical device which comprises electronics, battery, processor, and stimulatory circuitry. An electrode lead is connected to the implanted device, and carries a stimulus pulse to the distal end of the lead, where current may exit the lead through transducer contacts and enters the tissue that it is in contact with. Four to eight transducer contacts (electrodes) are included on existing deep-brain stimulators, while spinal simulators may have eight to 16 contacts per lead. It has not been possible to provide greater than eight transducer contacts electrodes on a deep brain stimulator lead; similarly, it has not been possible to provide greater than 16 transducer contacts (electrodes) on a spinal stimulator lead. This is because there is generally the requirement of one-to-one mapping of lead conductors (or wires) to output transducer contacts (electrode sites). Due to the constraints on the size (width or diameter) of the lead body, it has not been possible to accommodate more than 16 lead wires, which only allows for 16 transducer contacts. The small number of transducer contacts may lead to over-stimulation of non-target areas, which may result in severe side effects for the subject. These severe side effects may include difficulty with speech and memory loss. For spinal cord stimulation, lead migration after surgery reduces therapy effectiveness, which could be overcome by using the systems and methods of the present disclosure.

The control unit of the present disclosure alleviates the constraints associated with conventional equipment by placing a control unit within the lead body in close proximity to the transducer contacts. The control unit may be configured to have multiplexing functionality, which allows for a greater number of lead wires between the control unit and the transducer contacts. The diameter of the lead wires between the control unit and the transducer contacts, due to the shorter distance therebetween, may be much smaller than those used in conventional equipment. Thus, more wires, or filaments, may be accommodated, allowing for more transducer contacts to be used. In some embodiments of the invention, the transducer contacts of the present disclosure may have the same amount of surface area as the conventional equipment. However, the greater number of transducer contacts, which may be controlled individually, allows for finer control of the delivery of electrical signals to a desired or predetermined area.

In certain embodiments, a physiological electrical lead body is provided. The lead body may comprise a plurality of transducer contacts in close proximity to an end of the lead body. The lead body may also comprise a control unit positioned within the lead body in close proximity to the plurality of transducer contacts. The control unit may be in communication with the plurality of transducer contacts. The control unit may be constructed and arranged to enable precise delivery of signals to a predetermined treatment site. The control unit may comprise at least one electrical input contact and a plurality of electrical output contacts. The quantity of electrical input contacts is typically greater than the quantity of electrical output contacts.

In some embodiments, the diameter or width of the lead body is less than about 2 mm. In certain embodiments, the diameter or width of the lead body is less than about 2.0 mm. In other embodiments, the diameter or width of the lead body is less than about 1.3 mm. In specific examples, it may be 1.27 mm. The plurality of transducer contacts may comprise a quantity of transducer contacts to allow flexibility in the delivery of signals to a target site or a pretreatment area. The transducer contacts may be of a quantity to allow for precise delivery of signals to a predetermined target site. The precise delivery may be accomplished through the use of more transducer contacts in a given area than conventional devices. This higher density of transducer contacts allows for delivery of signals to smaller and more targeted areas. The plurality of transducer contacts may comprise at least about eight transducer contacts, but may be up to 64 transducer contacts, or higher. In some embodiments, the distance between the control unit and the end of the lead body is such that it allows for adequate reliability of the filaments between the control unit and the transducer contacts. In certain embodiments, the distance is less than about 5 cm and, in certain other embodiments, may be less than about 2 cm. The filaments may have a diameter of less than about 0.150 mm.

The transducer contacts may be in a form that allows them to transmit a signal. For example, a transducer contact may be in a form to transmit an electrical signal by way of an electrode contact. In another example, a transducer contact may be in a form to transmit an optic signal by way of an optical contact. The transducer contacts may be, for example electrode contacts, optical contacts, acoustic contacts, induction coil contacts, magnetic coil contacts, and combinations thereof. The plurality of transducer contacts may be referred to as an array of transducer contacts. Each transducer contact of the array may be the same type of contact; for example, each transducer contact may be an electrode contact. Alternatively, the array may include transducer contacts of more than one type. For example, the array may comprise alternating electrode contacts and optical contacts, or alternating electrode, optical and acoustic contacts. Any pattern of contacts may be used such that they may achieve a desired result of precisely targeting a particular treatment site of a subject. An array of transducer contacts may be processed by a control unit to present a waveform to an array of output signals.

The transducer contacts may also be in a form that allows them to perform one or more actions. The transducer contacts may be disposed to perform at least one of sensing at least one parameter of the physiological process, transmitting at least one parameter of the physiological process, stimulating the physiological process, or inhibiting the physiological process. In one embodiment, the control unit is constructed and arranged to record at least one parameter of the physiological process. For example, the transducer contacts may be at least one of a sensor, a recorder, a transmitter, a stimulator, and an inhibitor. Each transducer contact of an array may be the same type of transducer contact. For example, each transducer contact may be a stimulator. Alternatively, the array may include transducer contacts of more than one type. For example, the array may comprise alternating sensors and stimulators. In other examples, the array may comprise alternating sensors, stimulators, and recorders. Any pattern of contacts may be used such that they may achieve a desired result of precisely targeting a particular treatment site of a subject.

Parameters that may be sensed or transmitted may include electrical responses, blood pressure, heart rate, temperature, and pressure. Parameters may also include other physiological properties that may be useful in treatment of a subject or in diagnostic testing of a subject.

In some embodiments, the control unit of the system is configured to receive at least one first input signal from the implantable device and to transmit a plurality of output signals to the plurality of transducer contacts. The plurality of output signals may be based at least in part on the at least one first input signal from the implantable device and on a control function of the control unit. In some embodiments, the control unit is further configured to receive at least one signal from the plurality of transducer contacts, and the plurality of output signals is modulated in response to the at least one signal from the plurality of transducer contacts.

The electrical lead body may be configured to be connectable to an implantable device. The implantable device may comprise an energy source. The implantable device may be constructed and arranged to provide a signal.

In some embodiments, a method is provided for treating a condition in a subject. The method may comprise utilizing the control unit in the electrical lead body of the present disclosure. The method may comprise generating a first input signal from an implantable device. The method may further comprise transmitting the first input signal from the implantable device to a control unit positioned in an electrical lead body as described in this disclosure. A plurality of output signals may be generated based on the first input signal from the implantable device. The plurality of output signals may also be generated based on a control function of the control unit. The plurality of output signals may be transmitted from the control unit to a plurality of transducer contacts on the electrical lead body. This method may provide precise delivery of signals to a predetermined treatment site, for example, on a subject.

In some embodiments, the method may further comprise transmitting at least one second input signal from the plurality of transducer contacts to the control unit. In some embodiments, modulation of at least one parameter of the plurality of output signals in response to the at least one second input signal from the plurality of transducer contacts is performed. The at least one second input signal may be a plurality of second input signals. An array of transducer contacts, such as an array of sensors, may be utilized to provide a plurality of input signals from the plurality of transducer contacts to the control unit. This may present a waveform to an array of output signals. Recording of the at least one electrical signal from the plurality of electrode contacts may also be performed. In some embodiments, the electrode contacts of the control unit may perform at least one of sensing, transmitting, stimulating, and inhibiting. In some embodiments, the method may further comprises energizing the control unit from the implantable device.

As shown in FIG. 1, a portion of an electrical lead body 100 is provided. At an end of electrical lead body 100 a plurality of electrode contacts 102 and a control unit 104 is positioned. Electrical lead body may receive a signal through one or more wires 112 from a device, such as an implantable device, or another external source.

Figure 2A:
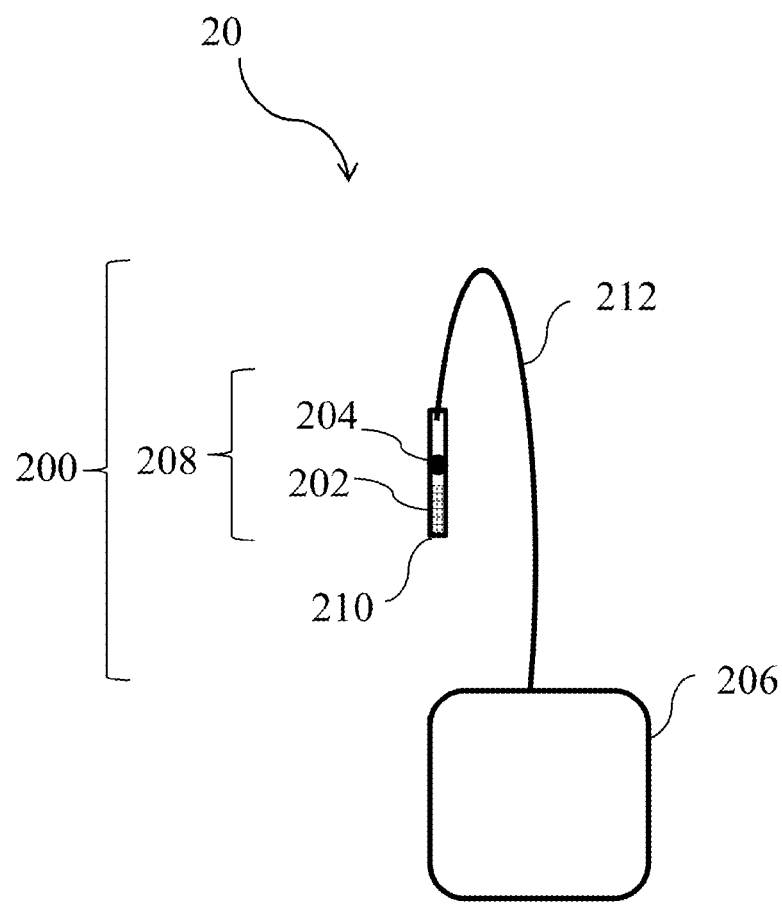
FIG. 2A is an illustration of a system in accordance with one or more aspects of the disclosure.

FIG. 2A shows system 20 for modulating a physiological process. Implantable device 206 may comprise a power source and a pulse generator and communicates by way of wires 212 in electrical lead body 200. Electrical lead body 200 comprises wires 212 and distal portion 208. Distal portion 208 comprises plurality of transducer contacts 202 which are in close proximity to distal end 210 of distal portion 208 of electrical lead body 200. Distal portion 208 also comprises control unit 204 which is positioned within electrical lead body 200 and in close proximity with plurality of transducer contacts 202. Control unit 204 is in communication with transducer contacts 202 and implantable device 206. At least a portion of distal portion 208 may be implanted into a subject, for example, a brain of a subject. Implantable device 206 may be implanted into any portion of the subject that would allow for appropriate operation of the device. For, example, implantable device 206 may be implanted into the subject's chest or in a portion of an ear, similar to a cochlear implant. Alternatively, implantable device 206 may also be constructed so that it may be affixed to the subject externally. Electrical lead body 212 may also be at least partially implantable within a subject.

Figure 2B:
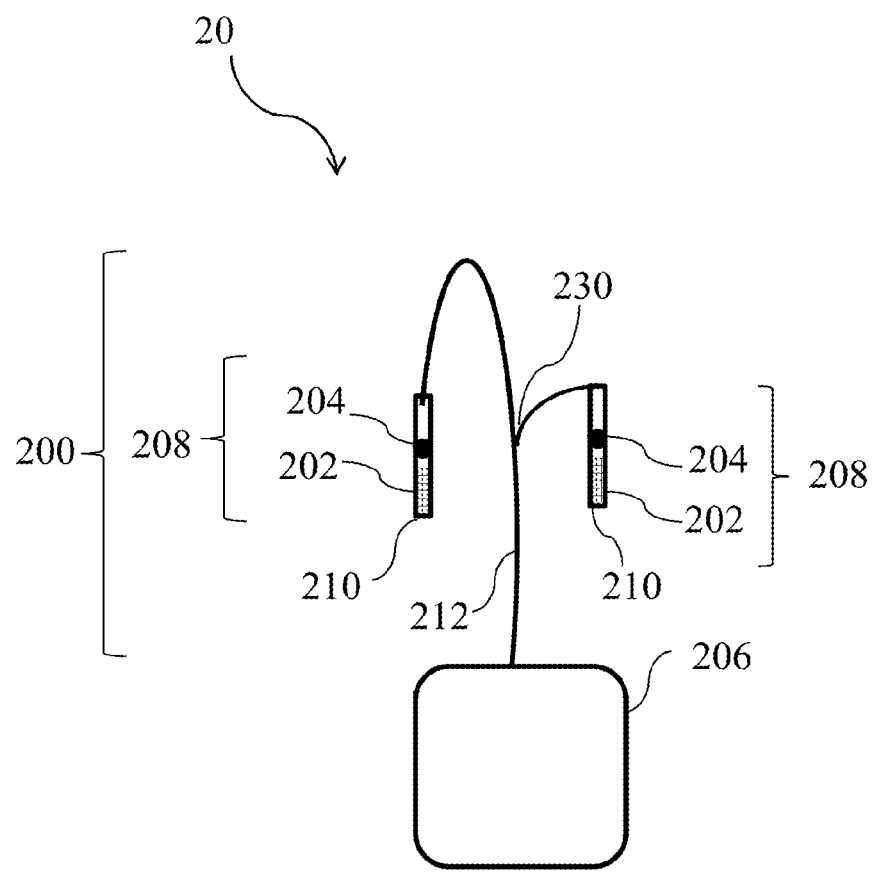
FIG. 2B is an illustration of a system in accordance with one or more aspects of the disclosure.

Additionally, as shown in FIG. 2B, more than one distal portion 208 may be in communication with implantable device 206 by way of wires 212. As shown in FIG. 2B, two distal portions 208 are shown, which are derived from lead body 212. Each distal portion 208 comprises control unit 204 which is positioned within electrical lead body 200 and in close proximity with plurality of transducer contacts 202. Each control unit 204 is in communication with transducer contacts 202 and implantable device 206. The bifurcation of wire 212 may occur anywhere along wire 212. Additionally, system 20 may comprise any number of distal portions 208 to provide the desired physiological effect.

Figure 2C:
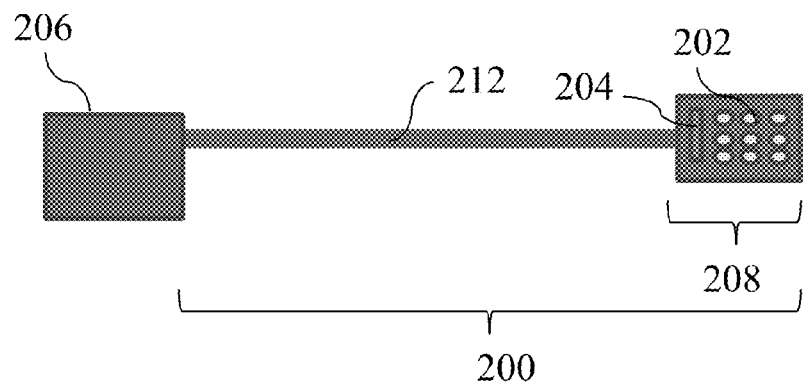
FIG. 2C is an illustration of a system in accordance with one or more aspects of the disclosure.
Figure 2D:
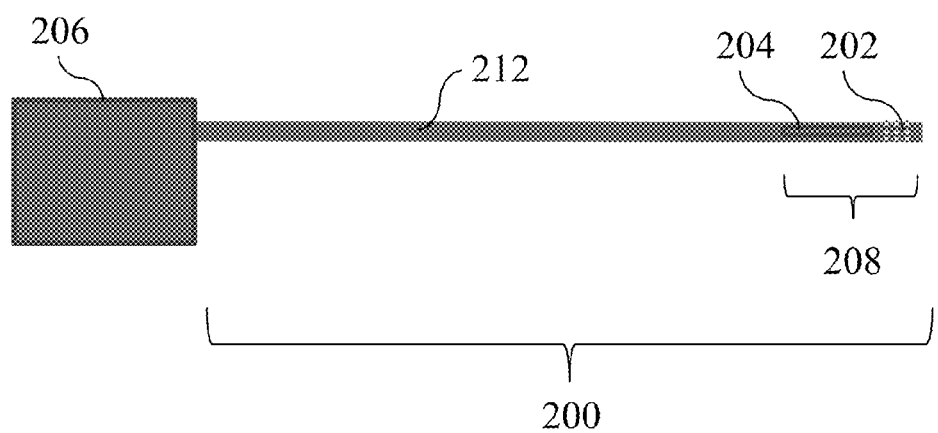
FIG. 2D is an illustration of a system in accordance with one or more aspects of the disclosure.

Distal portion 208 may be of various sizes and configurations to accommodate the target area of the subject. For example, in applications that include transmitting signals to the brain, the distal portion may be of a size to minimize disruption to the brain. In other applications, such as those related to spinal treatments, the distal portion may be of a greater width or height to accommodate the larger targeted area. This can be shown in FIG. 2C and FIG. 2D. As shown in FIG. 2C and FIG. 2D, system 20 for modulating a physiological process. Implantable device 206 may comprise a power source and a pulse generator and communicates by way of wires 212 in electrical lead body 200. Electrical lead body 200 comprises wires 212 and distal portion 208. Distal portion 208 comprises plurality of transducer contacts 202 which are in close proximity to distal end 210 of distal portion 208 of electrical lead body 200. Distal portion 208 also comprises control unit 204 which is positioned within electrical lead body 200 and in close proximity with plurality of transducer contacts 202. In certain embodiments, such as in spinal treatments, the configuration of FIG. 2C may be preferred. In other embodiments, such as treatments targeting the brain, the configuration of FIG. 2D may be preferred.

Figure 3A:
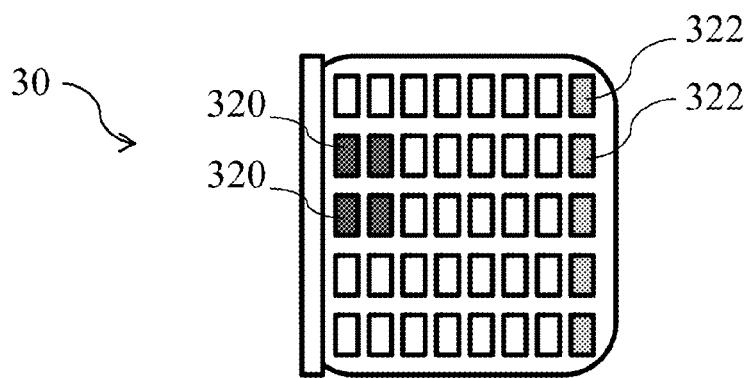
FIG. 3A is an illustration of a portion of a system in accordance with one or more aspects of the disclosure.
Figure 3B:
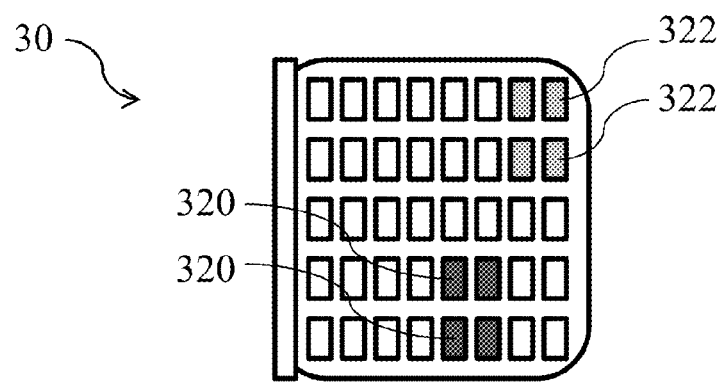
FIG. 3B is an illustration of a portion of a system in accordance with one or more aspects of the disclosure.
Figure 3C:
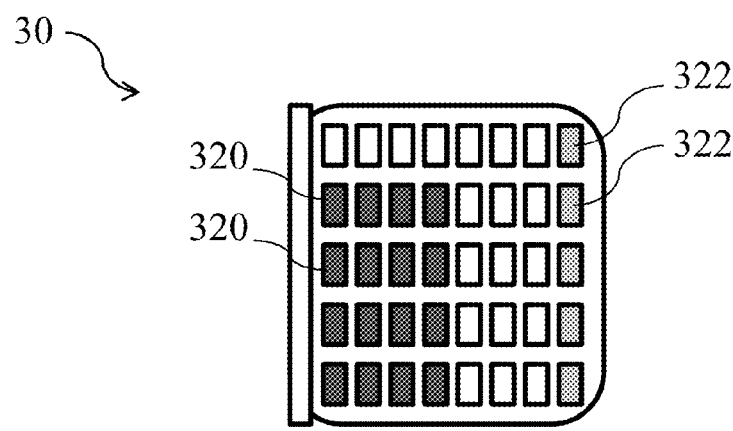
FIG. 3C is an illustration of a portion of a system in accordance with one or more aspects of the disclosure.

In certain embodiments, the system of the disclosure may be configured to deliver spatially targeted signals from array of transducer contacts 30. FIGS. 3A-3C exemplarily show a portion of the system for modulating a physiological process. The control unit may dynamically select or establish one transducer contact or a group or array of transducer contacts as a source of an output to the area to be treated. Transducer contacts may be selected from the group consisting of electrodes contacts, optical contacts, acoustic contacts, induction coil contacts, magnetic coil contacts, and combinations thereof.

For example, in FIG. 3A, dark grey transducers, including transducer contacts 320 may be electrode contacts that receive an output signal from the control unit and deliver the output signal to the treatment area. The output signal may function as a stimulus signal to stimulate the treatment area. Light grey transducers, including transducers 322, may be sensors that may sense a particular parameter of the treatment area and send one or more input signals to the control unit. The control unit may process the one or more input signals and, in response to the one or more sensor signals, may send one or more output signals back to transducers 320.

Alternatively, FIG. 3A may be a representative of an array comprising reference transducer contacts 322 and active transducer contacts 320 that deliver a pattern of stimulus from the control unit.

In certain embodiments, such as in FIG. 3A not all transducer contacts are in use at any given time. For example, in FIG. 3A, only eight of the 40 transducer contacts are in use, but more, less, none, or all of the transducer contacts may be in use at a given time, and this may change or stay the same during a given treatment.

FIG. 3B shows an alternate pattern of transducer contacts that may have been adjusted relative to the initial pattern. The adjustment may have been performed based on initial input signals from sensors 322 of FIG. 3A. The adjustment may also have been performed, in addition, or alternatively, based on a control function of the control unit. FIG. 3C shows an alternate pattern which may be based on input signals from sensors 322 of FIG. 3B. The adjustment may also have been performed, in addition, or alternatively, based on a control function of the control unit. Through adjustments of the spatial positioning and charge density of the transducer contacts, the electrical stimulation volume of the electrical lead can be carefully controlled to enable precise delivery of signals to a predetermined treatment area.

The disclosure is not limited in its application to the details of construction and arrangement of components, systems or subsystems set forth in the description, including the various examples or as illustrated in the drawings. The disclosure is capable of other embodiments and of being practiced or of being carried out in various ways. The terms used herein for the purpose of description should not be regarded as limiting. The use of the terms "comprising," "including," "carrying," "having," "containing," "involving," and the like are to be understood to be open-ended, that is, to mean including but not limited to. Only the transitional phrases "consisting of" and "consisting essentially of" shall be closed or semi-closed transitional phrases, respectively, as set forth, with respect to the claims.

Use of ordinal terms such as "first," "second," "third," and the like in the specification and claims to modify an element does not by itself connote any priority, precedence, or order of one element over another or the temporal order in which acts of a method are performed, but are used merely as labels to distinguish one element having a certain name from another element having a same name, but for use of the ordinal term, to distinguish the elements.

What is claimed is:

1. A system for modulating a physiological process, comprising:
    an implantable device comprising an energy source, the implantable device constructed and arranged to provide a signal; and
    an electrical lead body connected to the implantable device and comprising:
        a plurality of transducer contacts in close proximity to an end of the electrical lead body;
        a control unit positioned within the lead body in close proximity to the plurality of transducer contacts and constructed and arranged to enable precise delivery of signals to a predetermined treatment site, the control unit configured to receive at least one first input signal from the implantable device and to transmit a plurality of output signals to the plurality of transducer contacts, and further configured to receive at least one second input signal from the plurality of transducer contacts, the control unit comprising:
            at least one electrical input contact; and
            a plurality of electrical output contacts, wherein a quantity of the electrical output contacts is greater than a quantity of the electrical input contacts,
        wherein the plurality of output signals is modulated in response to the at least one second input signal from the plurality of transducer contacts, and the plurality of output signals is based at least in part on the at least one first input signal from the implantable device and on a control function of the control unit.

2. The system of claim 1, wherein the plurality of transducer contacts are disposed to perform at least one of sensing at least one parameter of the physiological process, transmitting at least one parameter of the physiological process, stimulating the physiological process, and inhibiting the physiological process.

3. The system of claim 2, wherein the control unit is constructed and arranged to record at least one parameter of the physiological process.

4. The system of claim 1, wherein a diameter of the electrical lead is less than about 2 mm.

5. The system of claim 1, wherein the plurality of transducer contacts comprises at least about 8 transducer contacts.

6. The system of claim 1, wherein a distance between the control unit and the end of the lead is less than about 5 cm.

7. The system of claim 1, wherein the control unit is encapsulated with a material.

8. The system of claim 7, wherein the encapsulation with the material provides a hermetic seal.

9. The system of claim 1, wherein the plurality of the electrical output contacts are connected to the plurality of transducer contacts by a plurality of filaments, each filament having a diameter of less than about 0.150 mm.

10. The system of claim 1, wherein the electrical lead is implantable in a subject.

11. The system of claim 1, wherein the implantable device provides power to the control unit to energize the control unit.

12. The system of claim 1, wherein the plurality of transducer contacts are selected from the group consisting of electrode contacts, optical contacts, acoustic contacts, induction coil contacts, magnetic coil contacts, and combinations thereof.

13. A method of treating a condition in a subject, comprising:
    generating a first input signal from an implantable device;
    transmitting the first input signal from the implantable device to a control unit positioned in an electrical lead body comprising a first end and a plurality of transducer contacts in close proximity to the first end;
    generating a plurality of output signals based on the first input signal from the implantable device and on a control function of the control unit;
    transmitting the plurality of output signals from the control unit to the plurality of transducer contacts to provide a precise delivery of signals to a predetermined treatment site;
    transmitting at least one second input signal from the plurality of transducer contacts to the control unit; and
    modulating at least one parameter of the plurality of output signals in response to the at least one second input signal from the plurality of transducer contacts.

14. The method of claim 13, further comprising recording the at least one second input signal from the plurality of transducer contacts.

15. The method of claim 13, wherein each of the plurality of transducer contacts performs the act of at least one of sensing, transmitting, stimulating, and inhibiting.

16. The method of claim 13, wherein the plurality of transducer contacts are selected from the group consisting of electrodes contacts, optical contacts, acoustic contacts, induction coil contacts, magnetic coil contacts, and combinations thereof.

17. The method of claim 13, further comprising energizing the control unit from the implantable device.

* * * * *